United States Patent
Nutaro et al.

(10) Patent No.: US 9,986,933 B2
(45) Date of Patent: Jun. 5, 2018

(54) NEUROPHYSIOLOGICAL-BASED CONTROL SYSTEM INTEGRITY VERIFICATION

(75) Inventors: Joseph J. Nutaro, Phoenix, AZ (US); Santosh Mathan, Seattle, WA (US); Steven P. Grothe, Cave Creek, AZ (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 1004 days.

(21) Appl. No.: 13/406,040

(22) Filed: Feb. 27, 2012

(65) Prior Publication Data
US 2013/0226023 A1 Aug. 29, 2013

(51) Int. Cl.
A61B 5/04 (2006.01)
A61B 5/0484 (2006.01)
A61B 5/048 (2006.01)

(52) U.S. Cl.
CPC ............ *A61B 5/0484* (2013.01); *A61B 5/048* (2013.01)

(58) Field of Classification Search
CPC ... A61B 5/0476; A61B 5/0482; A61B 5/0484; A61B 5/04842; A61B 5/04845; A61B 5/742
USPC .................................................. 600/544, 545
See application file for complete search history.

(56) References Cited

U.S. PATENT DOCUMENTS

| | | | |
|---|---|---|---|
| 5,687,291 A | 11/1997 | Smyth | |
| 5,788,648 A | 8/1998 | Nadel | |
| 5,899,867 A | 5/1999 | Collura | |
| 6,129,681 A | 10/2000 | Kuroda et al. | |
| 6,928,354 B2 | 8/2005 | Ryu et al. | |
| 7,546,158 B2 | 6/2009 | Allison et al. | |
| 2003/0176806 A1 | 9/2003 | Pineda et al. | |
| 2006/0133283 A1* | 6/2006 | Weiner et al. | 370/241 |
| 2006/0167371 A1* | 7/2006 | Flaherty et al. | 600/545 |
| 2006/0220498 A1* | 10/2006 | Kremer | 310/338 |
| 2008/0004500 A1* | 1/2008 | Cazares et al. | 600/300 |
| 2008/0208074 A1* | 8/2008 | Snyder et al. | 600/545 |
| 2008/0319275 A1* | 12/2008 | Chiu et al. | 600/300 |
| 2009/0322513 A1* | 12/2009 | Hwang et al. | 340/539.12 |
| 2010/0178640 A1 | 7/2010 | Yachin | |
| 2010/0217149 A1* | 8/2010 | Harrison et al. | 600/559 |
| 2010/0234752 A1* | 9/2010 | Sullivan et al. | 600/544 |
| 2011/0251511 A1 | 10/2011 | Desain et al. | |
| 2011/0298706 A1 | 12/2011 | Mann | |

OTHER PUBLICATIONS

Peiris,et al.; Detection of Lapses in Responsiveness from the EEG, IOP Publishing, Journal of Neural Engineering; J. Neural Eng. 8 (2011) 016003 (15pp).

* cited by examiner

*Primary Examiner* — Etsub Berhanu
(74) *Attorney, Agent, or Firm* — Lorenz & Kopf, LLP

(57) ABSTRACT

Methods and apparatus for verifying operability of a neurophysiological-based control system include generating a test stimulus that will result in a predetermined neurophysiological response in a user. Neurophysiological brain activity signals obtained from the user in response to the test stimulus are processed to generate a test neurophysiological response. The test neurophysiological response and a predetermined neurophysiological response are compared to determine if the neurophysiological-based control system is operating properly.

18 Claims, 4 Drawing Sheets

NEUROPHYSIOLOGICAL-BASED CONTROL SYSTEM INTEGRITY VERIFICATION

TECHNICAL FIELD

The present invention generally relates to neurophysiological-based control systems, and more particularly relates to systems and methods for verifying the integrity of a neurophysiological-based control system.

BACKGROUND

In recent years, various hands-free human-computer interface paradigms have been developed as alternatives to the conventional graphical user interface (GUI) paradigms. One such paradigm implements a neurophysiological based communication system. With this system, neurophysiological brain activity sensors, such as electroencephalogram (EEG) sensors, are disposed on a person, and stimuli are supplied to the person. The EEG sensors are used to identify a particular stimulus supplied to the user. The supplied stimulus may, for example, correspond to a particular command. This command may be used to move a component of a robotic agent.

In addition to neurophysiological-based human-computer interfaces described above, various other neurophysiological-based systems have been developed that rely on real-time EEG-based sensing. These other systems may be used to, for example, monitor working memory, attention, and assist in target detection in image collections.

Although the neurophysiological-based systems described above present potential improvements over current technology paradigms, the systems that have been developed thus far have limited capabilities. This is due, in part, to the lack of system integrity verification to ensure the system is operating properly. More specifically, presently known neurophysiological-based systems do not implement any type of periodic or continuous monitoring capability verify that the system is operating properly. Rather, present neurophysiological-based systems employ checks of impedance and general electrical connectivity.

Hence, there is a need for a system and method that identifies whether the integrity of the system from the sensor connection through the signal processing chain is effective. In other words, that verifies that the system integrity is sufficiently sound to detect neural activity. The present invention addresses at least this need.

BRIEF SUMMARY

In one embodiment, a method for verifying operability of a neurophysiological-based control system includes generating a test stimulus that will result in a predetermined neurophysiological response in a user, processing neurophysiological brain activity signals obtained from the user in response to the test stimulus, to thereby generate a test neurophysiological response, and comparing the test neurophysiological response and a predetermined neurophysiological response to determine if the neurophysiological-based control system is operating properly.

In another embodiment, a neurophysiological-based control system includes a test stimulus source, a neurophysiological brain sensor, and a processor. The test stimulus source is configured to at least selectively generate and supply a test stimulus that will result in a predetermined neurophysiological response in a user. The neurophysiological brain sensor is configured to obtain and supply a plurality of neurophysiological brain activity signals from the user when the user is receiving the test stimulus. The processor is coupled to receive the neurophysiological brain activity signals and is configured, in response thereto, to generate a test neurophysiological response and compare the test neurophysiological response and a predetermined neurophysiological response to determine if the neurophysiological-based control system is operating properly.

Furthermore, other desirable features and characteristics of the integrity verification system and method will become apparent from the subsequent detailed description and the appended claims, taken in conjunction with the accompanying drawings and the preceding background.

BRIEF DESCRIPTION OF THE DRAWINGS

The present invention will hereinafter be described in conjunction with the following drawing figures, wherein like numerals denote like elements, and wherein.

DETAILED DESCRIPTION

The following detailed description is merely exemplary in nature and is not intended to limit the invention or the application and uses of the invention. As used herein, the word "exemplary" means "serving as an example, instance, or illustration." Thus, any embodiment described herein as "exemplary" is not necessarily to be construed as preferred or advantageous over other embodiments. All of the embodiments described herein are exemplary embodiments provided to enable persons skilled in the art to make or use the invention and not to limit the scope of the invention which is defined by the claims. Furthermore, there is no intention to be bound by any expressed or implied theory presented in the preceding technical field, background, brief summary, or the following detailed description.

Figure 1:
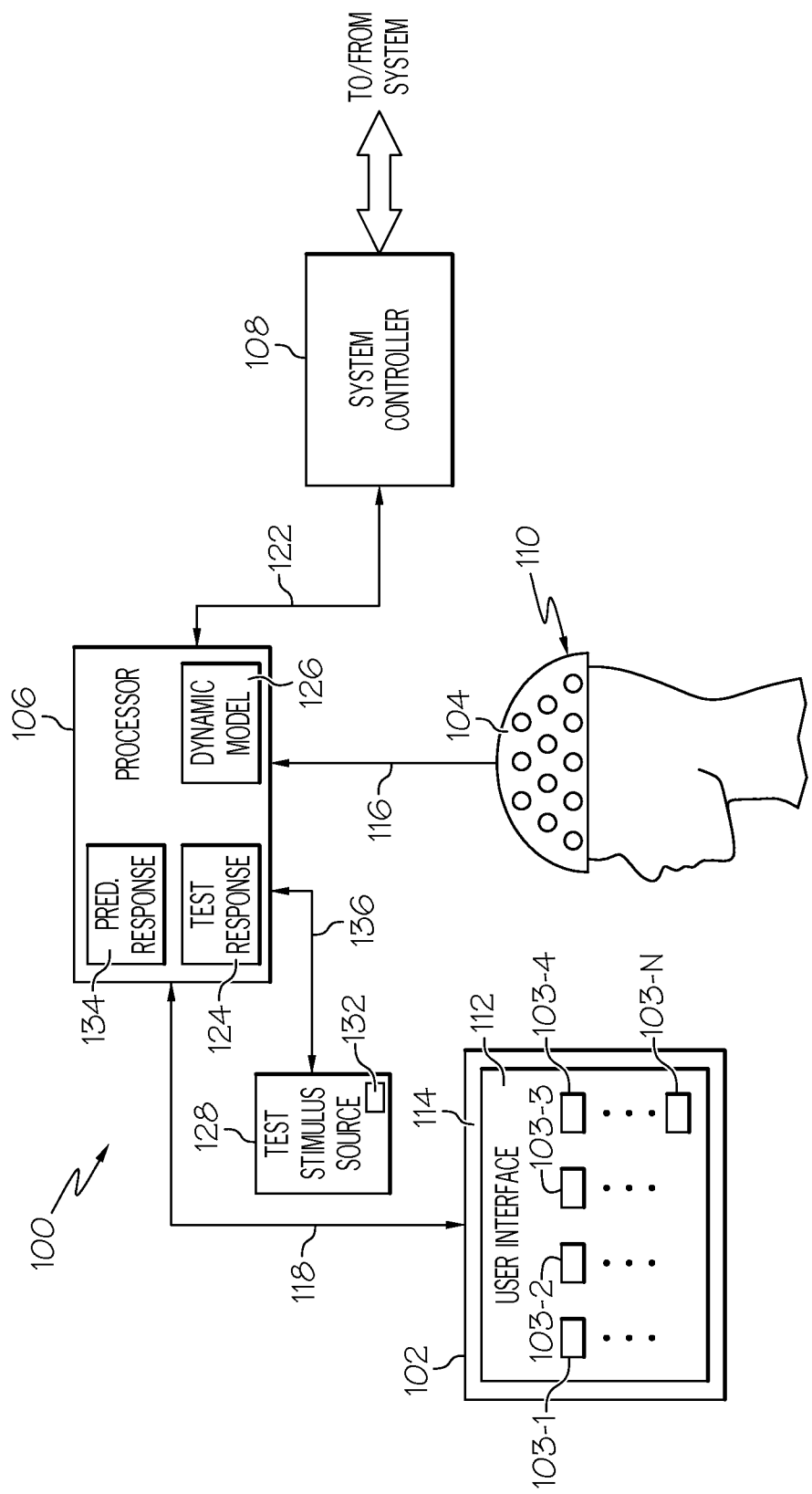
FIG. 1 depicts a functional block diagram of one embodiment of a thought-enabled hands-free control system for controlling a multiple degree-of-freedom system.

Referring to FIG. 1, a functional block diagram of a neurophysiological-based control system 100 is depicted and includes a user interface 102, a neurophysiological brain activity sensor 104, a processor 106, and a system controller 108. The user interface 102 is configured to supply a plurality of user stimuli 103 (e.g., 103-1, 103-2, 103-3, . . . 103-N) to a user 110. The user interface 102 and user stimuli 103 may be variously configured and implemented. For example, the user interface 102 may be a visual interface, a tactile interface, an auditory interface or various combinations thereof. As such, the user stimulus 103 supplied by the user interface may be a visual stimulus, a tactile stimulus, an auditory stimulus, or various combinations thereof. In the depicted embodiment, however, the user interface 102 is a visual user interface and the user stimuli 103 are all implemented as visual stimuli.

Figure 2:
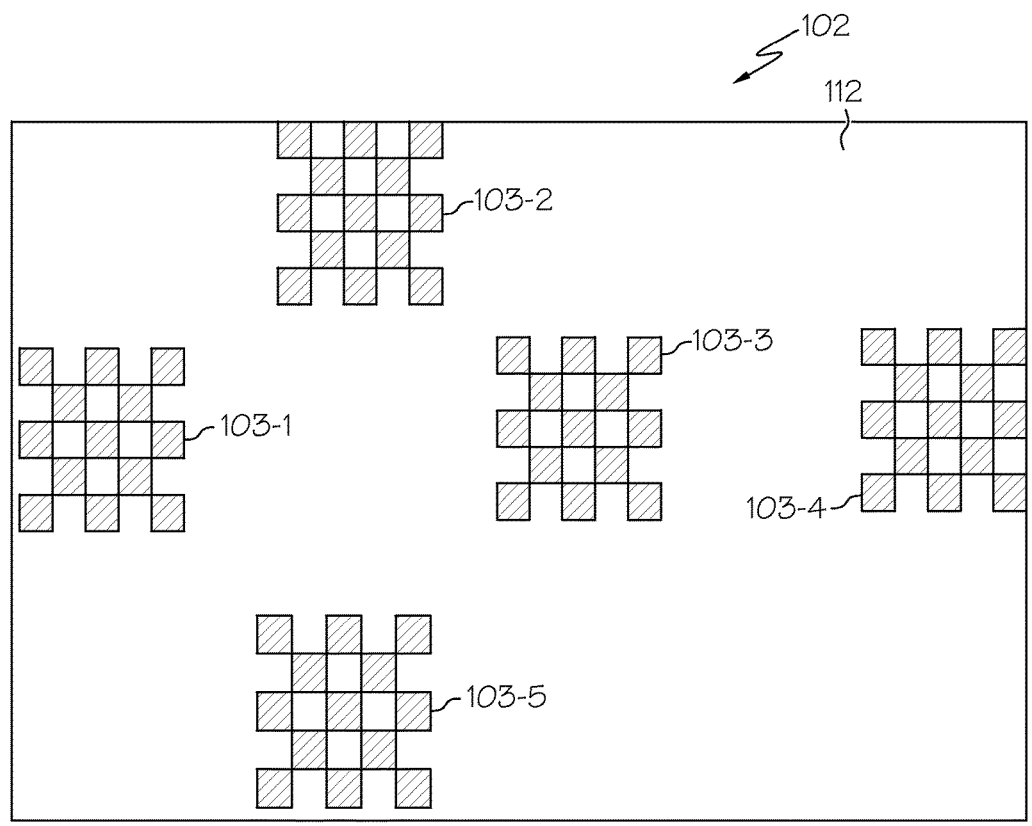
FIG. 2 depicts an example of how visual stimuli may be presented to a user on a visual user interface.

As may be appreciated, the visual user interface 102 may be variously configured and implemented. For example, it may be a conventional display device (e.g., a computer monitor), an array of light sources, such as light emitting diodes (LEDs), that may be variously disposed on the visual user interface 102. The user stimuli 103 may also be variously implemented. For example, each user stimulus 103 may be rendered on a display portion 112 of the visual user interface 102 as geometric objects and/or icons, or be implemented using spatially separated lights disposed along a peripheral 114 or other portion of the visual user interface 102, or a combination of both. One example of how visual stimuli 103 may be presented to a user on the visual user interface 102 is depicted in FIG. 2. No matter how the user interface 102 and user stimuli 103 are specifically implemented, each user stimulus 103 represents a command.

The neurophysiological brain activity sensor 104 is configured to sense the neurophysiological brain activity of the user 110, and to supply neurophysiological brain activity signals 116 representative thereof. In the embodiment depicted in FIG. 1, the neurophysiological brain activity sensor 104 is configured to be disposed on, or otherwise coupled to, the user 110, and is implemented using a plurality of electroencephalogram (EEG) sensors 104. It will be appreciated that EMG (electromyogram) sensors could also be used. The EEG sensors 104 are configured to be disposed on or near the head of the user 110 by, for example, embedding the EEG sensors 104 in a helmet or cap. The neurophysiological brain activity sensor 104 may additionally be configured to sense various types of neurophysiological brain activity, and thus supply various types of neurophysiological brain activity signals 116. For example, the neurophysiological brain activity sensor 104 may be configured to sense, and supply signals representative of, event related potentials (ERPs), steady state visual evoked response potentials (SSVEPs), or alpha waves. Before proceeding further, a brief discussion of each of these brain activity measures will be provided.

Figure 3:
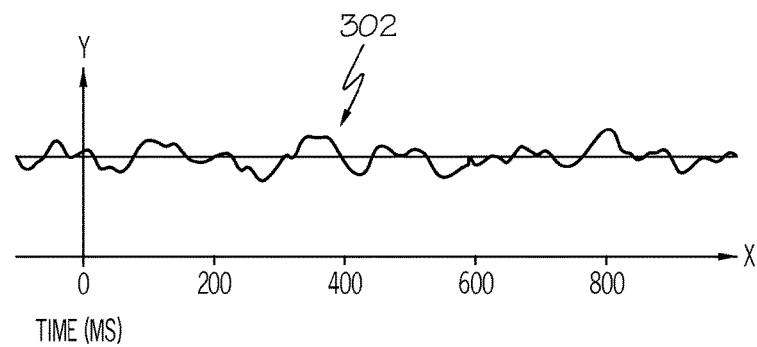
FIG. 3 depicts an exemplary electroencephalogram (EEG) signal supplied from a single EEG electrode in response to a task-irrelevant stimulus.
Figure 4:
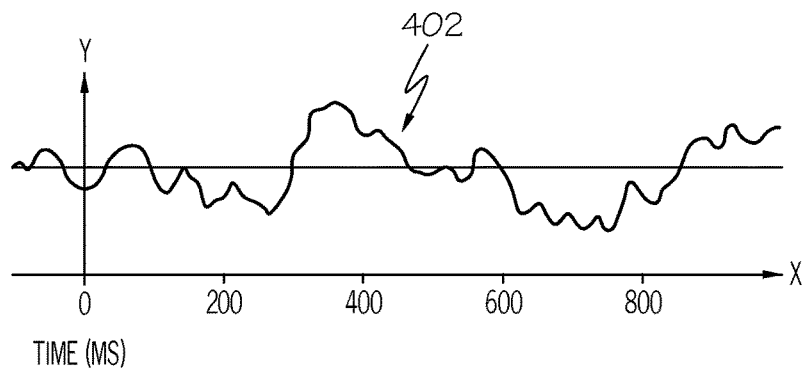
FIG. 4 depicts an exemplary EEG signal supplied from the single EEG electrode in response to a task-relevant stimulus.

An ERP refers to a morphological change in an EEG waveform in response to a task-relevant stimulus, and typically occurs within several hundred milliseconds of the task-relevant stimulus. As an example, FIG. 3 depicts an exemplary baseline EEG signal 302 supplied from a single EEG sensor, and FIG. 4 depicts an exemplary EEG signal 402 supplied from the same EEG sensor in response to a task-relevant stimulus. The x-axis in both FIGS. 3 and 4 depicts the progression of time, in milliseconds, following the onset of a stimulus, which occurs at the time-zero point. As may be readily seen, the EEG signal 402 following the task-relevant stimulus exhibits a pronounced amplitude perturbation within a few hundred milliseconds of stimulus onset. It is noted that a task-relevant stimulus may be, for example, displaying an image with a target (e.g., a specific letter, number, object, etc.), and a task-irrelevant image may be, for example, displaying an image without a target.

Figure 5:
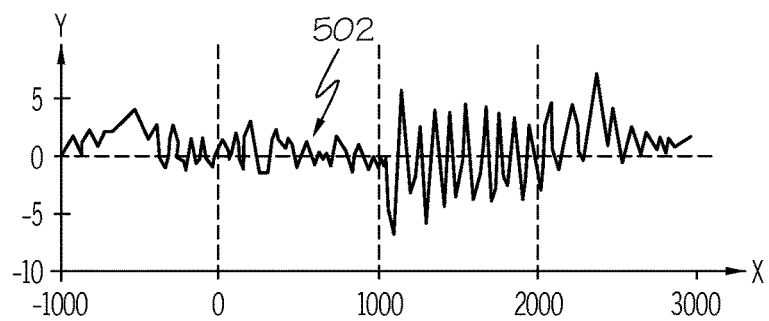
FIG. 5 depicts an exemplary EEG signal supplied from a single EEG electrode in response to an oscillating visual stimulus.

An SSVEP is a harmonic neural response to an oscillating visual stimulus. For example, when a user 110 views a stimulus of a particular frequency, a cluster of neurons in the visual areas of the user's brain (at the back of the head) fire synchronously at the same frequency, and generate a neural signal that is generally referred to as a steady state visual evoked response potential (SSVEP). Thus, as depicted in FIG. 5, when the user 110 views a light or image flashing at 10 Hz, this cluster of neurons fires synchronously at 10 Hz, and an EEG signal 502 supplied from a single EEG sensor oscillates at the 10 Hz, too. The SSVEP signal is robust, consistent across individuals, and can be detected by a relatively small number of EEG sensors.

Figure 6:
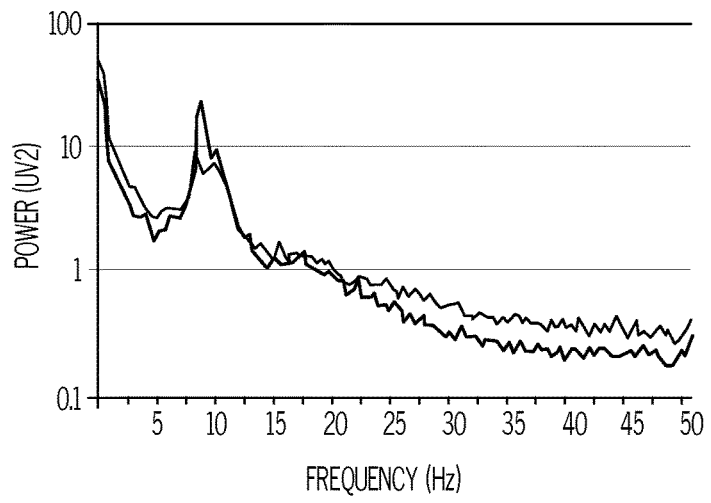
FIGS. 6 and 7 depict exemplary alpha rhythm signals supplied from a single EEG electrode with a user's eyes closed and a user's eyes open, respectively.
Figure 7:
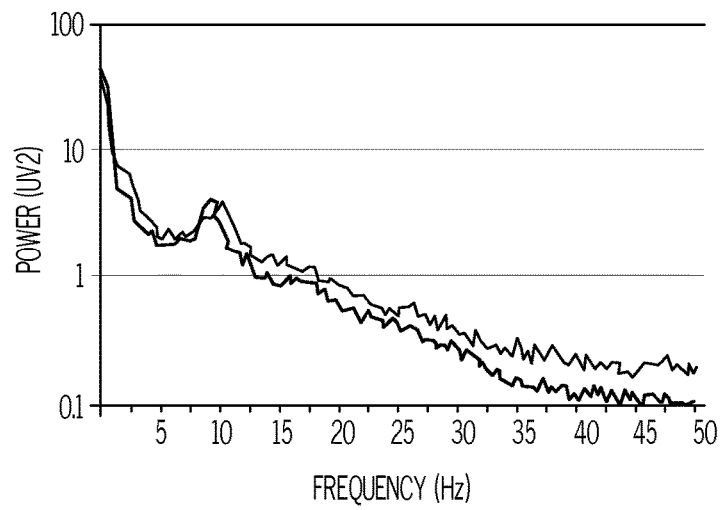

Alpha waves are synchronous oscillations in the 8-12 Hz range over the visual cortex, and are indicators of the visual system in an idle state. As is generally known, alpha waves are most prominent when a user has their eyes closed. However, as depicted in FIGS. 6 and 7, alpha waves can be observed in an averaged EEG power spectrum whether or not a user has their eyes closed. As such, the presence or absence of alpha waves can be used for those users 110 that demonstrate prominent alpha signatures.

Returning to FIG. 1, and to the remaining description of the system 100, it is seen that the processor 106 is in operable communication with the user interface 102 and the neurophysiological brain activity sensor 104 via, for example, one or more communication buses or cables 118. The processor 106 is coupled to receive the neurophysiological brain activity signals 116 from the neurophysiological brain activity sensor 104. The processor 106 is configured, upon receipt of the neurophysiological brain activity signals 116, to generate a neurophysiological response signal. The neurophysiological response signal that the processor 106 generates will be either a system command 122 or, as will be described further below, a test neurological response 124. When the user interface 102 is the source of stimulus to the user 110, then the processor 106 will generate a system command. The manner in which the processor 106 will generate a test neurophysiological response 124 will be described further below.

Before proceeding further, it is noted that the processor 106 may implement its functionality using any one of numerous techniques. For example, the processor 106 may be configured to implement any one of numerous known non-model based classifiers, such as template matching, linear, or quadratic discriminant. In the depicted embodiment, the processor 106 is configured to implement a dynamic model 126 that represents the dynamic behavior of the user 110 in response to stimuli supplied to the user 110.

The dynamic model 126 is generated using calibration data obtained from the user 110. The dynamic model 126 may thus be custom fitted to each individual user by using various system identification techniques. Some non-limiting examples of suitable techniques include least-squares regression and maximum likelihood model fitting procedures. The dynamic model 126 may be either linear or non-linear dynamic models. Some non-limiting examples of suitable dynamic models include finite impulse response (FIR) filters, finite-dimensional state linear models, finite-dimensional state nonlinear models, Volterra or Wiener series expansions, and kernel regression machines.

The dynamic model 126 is also used to develop statistical (Bayesian) intent classifiers. The model-based classifiers can be designed to be generative or discriminative. An example of a suitable generative classifier is the minimum Bayesian risk classifier that uses dynamic and statistical models of the brain activity signals 116 in response to different stimuli. An example of a suitable discriminative classifier is a support vector machine that uses, for example, the Fisher kernel obtained from this system model.

Figure 8:
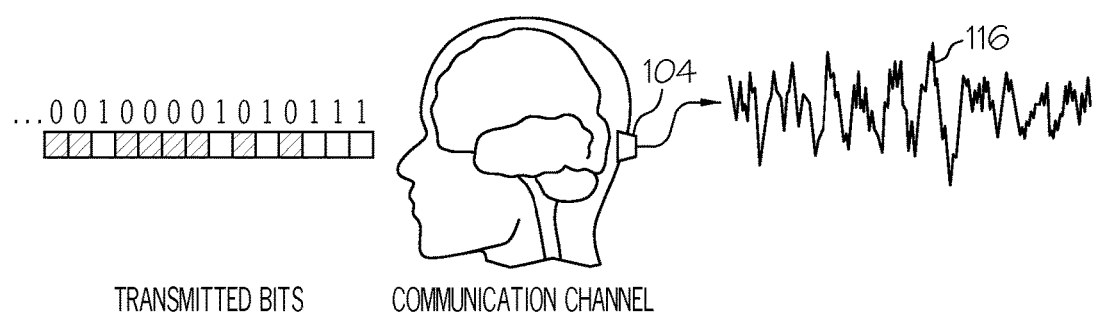
FIG. 8 depicts a simplified representation of a model of a human visual system as a communications channel.

One particular advantage of using the dynamic model 126 is that it may also be thought of as a communication channel through which bits representative of possible commands are transmitted. This concept is illustrated in FIG. 8. As such, information theory and modern coding theory used in digital communications may be employed. In particular, different stimulus patterns (or coding schemes) for each user stimulus 103 may be developed in order to achieve relatively higher, error-free bandwidths that approach the theoretical Shannon capacity of the communication channel. The dynamic model 126 associated with each user 110 will determine the optimal coding scheme. One particular example of a suitable coding scheme is the phase-shifted m-sequences.

The processor 106 may be variously implemented, and may include one or more microprocessors, each of which may be any one of numerous known general-purpose microprocessors or application specific processors that operate in response to program instructions. It will additionally be appreciated that the processor 106 may be implemented using various other circuits, not just one or more programmable processors. For example, digital logic circuits and analog signal processing circuits could also be used. It is further noted that the processor 106 may also implement various signal processing techniques. These signal processing techniques may vary, and may include one or more of DC drift correction and various signal filtering. The filtering may be used to eliminate noise and various other unwanted signal artifacts due to, for example, noise spikes, muscle artifacts, and eye-blinks.

No matter how the processor 106 specifically implements its functionality, the system command signals 122 it generates are supplied to the system controller 108. The system controller 108 is configured, upon receipt of each system command signal 122, to generate one or more component commands that cause a system (not depicted in FIG. 1) to implement the system command. The system controller 108 is, more specifically, configured to map each received system command signal 122 to one or more component commands, and to transmit the one or more component commands to one or more components. The one or more components, in response to the component command each receives, implements the component command, and together these components cause the system to implement the system command.

In addition to the above, the depicted neurophysiological-based control system 100 is configured to implement system integrity verification. To do so, the system 100 additionally includes a test stimulus source 128 and, as noted above, the processor 106 is additionally configured to at least selectively generate test neurological response signals 124. The test stimulus source 128 is configured to at least selectively generate and supply a test stimulus 132 to the user 110. That is, the test stimulus source 128 may be configured to generate and supply the test stimulus 132 periodically, continuously, or in response to an input command from the user 110. The test stimulus source 128, and thus the test stimulus 132, may also be variously implemented. For example, the test stimulus source 128 may be a visual interface, a tactile interface, an auditory interface or various combinations thereof. As such, the test stimulus 132 supplied by the test stimulus source 128 may be a visual stimulus, a tactile stimulus, an auditory stimulus, or various combinations thereof.

It will additionally be appreciated that in some embodiments, the test stimulus source 128 may also be implemented using systems and/or devices that comprise the system 100 or are inherent in the task environment in which the system 100 is disposed. For example, the test stimulus source 128 may comprise user interface 102, another non-illustrated display, another non-illustrated source of aural or tactile stimulus. In such embodiments, the test stimulus may be associated with inherent functions of such systems/devices. For example, the test stimulus 132 could be the flicker associated with the refresh rate of a display, or messages and alerts that are an integral part of the task environment. No matter its specific configuration and implementation, the test stimulus 132 generated and supplied by the test stimulus source 128 is one that will result in a predetermined neurophysiological response in the user 110.

The neurophysiological response of the user 110 to the test stimulus 132 is sensed by the neurophysiological brain activity sensor 104. The neurophysiological brain activity sensor 104, as noted above, supplies neurophysiological brain activity signals 116 representative of the neurophysiological response to the processor 106. The processor 106 is configured, in response to the neurophysiological brain activity signals 116 that result from the test stimulus 132, to generate the test neurological response 124. The processor 106 is further configured, based on the test neurological response 124, to determine if the neurophysiological-based control system is operating properly. Although this functionality may be variously implemented, the depicted processor 106 is configured to determine if the neurophysiological-based control system 100 is operating properly by comparing the test neurophysiological response 124 and a predetermined neurophysiological response 134, which may be stored in a non-illustrated memory.

The integrity of the system 100 may also be verified by commanding a response in the test stimulus source 128. That is, the user 110, either voluntarily or in response to a prompt, may supply themselves with an appropriate input test stimulus. The input test stimulus, which may be visual, aural, tactile, or various combinations thereof, will result in the user 110 supplying neurophysiological brain activity signals 116 representative of a test command for the test stimulus source 128. The processor 106, in response to these signals, will generate and supply a test command 136 to the test stimulus source 128. The processor 106 may then determine if the neurophysiological-based control system 100 is operating properly based on the response of the test stimulus source 128 to the test command 136.

Another technique that the neurophysiological-based control system 100 may implement to verify its integrity is for the user 110, either voluntarily or in response to a prompt, to supply neurophysiological brain activity signals 116 representative of a system command. The processor 106, in response to these signals, will generate and supply a system command to the system controller 108. The user 110 may then determine if the neurophysiological-based control system 100 is operating properly based on the response of the system controller 108, and the one or more components being controlled by the system controller 108, to the system command. The processor 106 could be configured such that the user 110 may have to reverse the completed command, or it could be configured to generate a system command that automatically reverses the user-initiated command.

The continuous or periodic test in which the test stimulus source 132 supplies a test stimulus, verifies the integrity of the brain activity sensor 104 and processor 106, as will the test in which the user commands a response in the test stimulus source 132. The test in which the user commands a system response, will verify the integrity of the overall neurophysiological-based control system 100. In any of these instances, it is noted that the processor 106 is further configured to generate an alert signal when it determines that all or a portion the system 100 is not operating properly. The alert signal may be used to generate an aural, visual, or tactile alert to the user 110. Moreover, the system 100 may additionally be configured, upon determining that all or a portion the system 100 is not operating properly, to implement one or more other functions. For example, the operational mode of the system may change, the system may identify the source of the problem, and/or the system may log problem.

Those of skill in the art will appreciate that the various illustrative logical blocks, modules, circuits, and algorithm steps described in connection with the embodiments disclosed herein may be implemented as electronic hardware, computer software, or combinations of both. Some of the embodiments and implementations are described above in terms of functional and/or logical block components (or modules) and various processing steps. However, it should be appreciated that such block components (or modules) may be realized by any number of hardware, software, and/or firmware components configured to perform the specified functions. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. For example, an embodiment of a system or a component may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments described herein are merely exemplary implementations.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal, or in a cloud-based computing platform.

In this document, relational terms such as first and second, and the like may be used solely to distinguish one entity or action from another entity or action without necessarily requiring or implying any actual such relationship or order between such entities or actions. Numerical ordinals such as "first," "second," "third," etc. simply denote different singles of a plurality and do not imply any order or sequence unless specifically defined by the claim language. The sequence of the text in any of the claims does not imply that process steps must be performed in a temporal or logical order according to such sequence unless it is specifically defined by the language of the claim. The process steps may be interchanged in any order without departing from the scope of the invention as long as such an interchange does not contradict the claim language and is not logically nonsensical.

Furthermore, depending on the context, words such as "connect" or "coupled to" used in describing a relationship between different elements do not imply that a direct physical connection must be made between these elements. For example, two elements may be connected to each other physically, electronically, logically, or in any other manner, through one or more additional elements.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method for verifying operability of a neurophysiological-based control system, comprising the steps of:
   generating, in a test stimulus source, a test stimulus that will result in a predetermined neurophysiological response in a user;
   processing, in a processor, neurophysiological brain activity signals obtained from the user in response to the test stimulus, to thereby generate a test neurophysiological response;
   comparing, in the processor, the test neurophysiological response and a predetermined neurophysiological response to determine if the neurophysiological-based control system is operating properly; and
   when a determination is made, in the processor, that the neurophysiological-based control system is not operating properly: (1) generating an alert, (2) generating a log file record, and (3) reverting operation to an alternate system.

2. The method of claim 1, further comprising:
   processing, in the processor, neurophysiological brain activity signals obtained from the user to thereby generate a test command; and
   supplying the test command to the test stimulus source; and
   determining, in the processor, if the neurophysiological-based control system is operating properly based on the response of the test stimulus source to the test command.

3. The method of claim 1, further comprising:
processing, in the processor, neurophysiological brain activity signals obtained from the user to thereby generate a system command;
supplying the system command to a system controller; and
determining, in the processor, if the neurophysiological-based control system is operating properly based on the response of the system controller to the system command.

4. The method of claim 1, wherein the test stimulus is generated periodically.

5. The method of claim 1, wherein the test stimulus is generated continuously.

6. The method of claim 1, wherein the step of generating a test stimulus comprises generating a visual stimulus.

7. The method of claim 1, wherein the step of generating a test stimulus comprises generating an aural stimulus.

8. The method of claim 1, wherein the step of generating a test stimulus comprises generating a tactile stimulus.

9. The method of claim 1, wherein:
the neurophysiological-based control system is disposed within a task environment; and
the step of generating a test stimulus comprises utilizing one or more stimuli inherent in the task environment.

10. The method of claim 1, wherein the step of processing neurophysiological brain activity signals comprises:
sensing steady state visual evoked response potentials (SSVEPs); and
processing the SSVEPs to generate the test neurophysiological response.

11. The method of claim 1, wherein the step of processing neurophysiological brain activity signals comprises:
sensing event-related potentials (ERPs); and
processing the ERPs to generate the test neurophysiological response.

12. The method of claim 1, wherein the step of processing neurophysiological brain activity signals comprises:
sensing alpha waves; and
processing the alpha waves to generate the test neurophysiological response.

13. A neurophysiological-based control system, comprising:
a test stimulus source configured to at least selectively generate and supply a test stimulus that will result in a predetermined neurophysiological response in a user;
a neurophysiological brain sensor configured to obtain and supply a plurality of neurophysiological brain activity signals from the user when the user is receiving the test stimulus; and
a processor coupled to the neurophysiological brain sensor to receive the neurophysiological brain activity signals therefrom and configured, in response thereto, to (i) generate a test neurophysiological response, (ii) compare the test neurophysiological response and a predetermined neurophysiological response to determine if the neurophysiological-based control system is operating properly, and (iii) upon determining that the neurophysiological-based control system is not operating properly, to:
generate an alert,
generate a log file record, and
revert operation to an alternate system.

14. The system of claim 13, wherein:
the system further comprises a system controller coupled to receive system commands and responsive thereto to generate one or more component commands;
the processor is further configured to:
process neurophysiological brain activity signals and generate the system commands;
monitor the response of the system controller to the system commands; and
determine if the neurophysiological-based control system is operating properly based on the response of the system controller to the system command.

15. The system of claim 13, wherein the test stimulus source is configured to generate one or more of a visual stimulus, an aural stimulus, and a tactile stimulus.

16. The system of claim 13, wherein neurophysiological brain activity sensor is configured to sense steady state visual evoked response potentials (SSVEPs).

17. The system of claim 13, wherein neurophysiological brain activity sensor is configured to sense event-related potentials (ERPs).

18. The system of claim 13, wherein neurophysiological brain activity sensor is configured to sense alpha waves.

* * * * *